United States Patent [19]

Austin et al.

[11] Patent Number: 5,074,911
[45] Date of Patent: Dec. 24, 1991

[54] HETEROCYCLIC THIONE

[75] Inventors: Peter W. Austin, Bury; Peter M. Quan, Rochdale; Peter A. Tasker, Dobcross; Derek Thorp, Hopwood, all of England

[73] Assignees: Imperical Chemical Industries PLC, London, England; Nerco Inc., Portland, Oreg.

[21] Appl. No.: 544,282

[22] Filed: Jun. 26, 1990

[30] Foreign Application Priority Data

Jul. 12, 1989 [GB] United Kingdom ................. 8915959

[51] Int. Cl.$^5$ ................................................ C22B 3/00
[52] U.S. Cl. ........................................ 75/743; 75/722; 423/DIG. 14; 423/131; 423/112
[58] Field of Search ............... 423/DIG. 14, 112, 131; 75/722, 743

[56] References Cited

U.S. PATENT DOCUMENTS

| 3,971,843 | 6/1976 | Helgorsky et al. | 423/112 |
| 4,169,130 | 11/1979 | Helgorsky et al. | 423/112 |
| 4,241,029 | 12/1980 | Helgorsky et al. | 423/112 |
| 4,292,284 | 11/1981 | Tomil et al. | 423/112 |
| 4,369,166 | 1/1983 | Leveque et al. | 423/112 |
| 4,372,923 | 2/1983 | Helgorsky et al. | 423/112 |
| 4,485,076 | 11/1984 | Bauer et al. | 423/112 |
| 4,559,203 | 12/1985 | Bauer et al. | 423/112 |
| 4,639,355 | 1/1987 | Matsui et al. | 423/DIG. 14 |
| 4,724,129 | 2/1988 | Helgorsky | 423/112 |

FOREIGN PATENT DOCUMENTS 1253976 8/1986 U.S.S.R. .

Primary Examiner—Theodore Morris
Assistant Examiner—Edward Squillante
Attorney, Agent, or Firm—William E. Dickheiser

[57] ABSTRACT

A process for extracting metal values such as gallium and/or indium from aqueous solutions by contacting said solutions with a water immiscible organic solvent having dissolved therein a heterocyclic thione.

6 Claims, No Drawings

HETEROCYCLIC THIONE

SUMMARY OF THE INVENTION

This specification describes an invention relating to an organic compound suitable for use in the purification of certain metals by formation of a complex with the metals and extraction from an aqueous phase into a solvent and to processes for the extraction of a metal from an aqueous phase into an organic phase and for the re-extraction (stripping) of the metal into an aqueous phase.

DETAILED DESCRIPTION OF THE INVENTION

According to the present invention there is provided a heterocyclic thione of the Formula I:

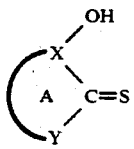  (I)

wherein
X is C and Y is N—R;
or X is N and Y is C—R, N, N—R, O or S;
each R is independently H or a substituent which does not interfere with stripping or extraction;
and A is a mono or bicyclic system, including the group —X(OH)—CS—Y—, carrying one or more aliphatic hydrocarbyl groups containing a total of from 6-40 carbon atoms.

Where A is monocyclic it is preferably a 5- or 6-membered ring containing up to three heteroatoms selected from nitrogen, sulphur and oxygen. Examples of such rings are dihydropyridothione, dihydropyrazothione, dihydropyrimidothione, dihydropyridazathione, dihydropyrazolothione, dihydrothiazolothione, dihydroisothiazolothione, dihydrothiadiazolothione, dihydrooxazolothione, dihydrooxadiazolothione, dihydroimidazolothione and dihydrotriazolothione. Where A is bicyclic it is preferably two fused 6-membered rings or fused 5- and 6-membered rings, such as benzofused analogues of the above mentioned rings, especially, dihydroquinolothione, dihydrobenzothiazolothione, dihydrobenzopyrazolothione, dihydrobenzoimidazolothione, dihydrobenzoisothiazolothione and dihydropyridoisothiazolothione.

The inert substituents, represented by R, can be any groups which do not significantly interfere with the action of the molecule in complexing with the metal, seriously impair its solubility in non-polar solvents or significantly enhance its solubility in water. One or more of these may be, or contain, the hydrocarbyl group, as hereinafter described. Examples of other inert substituents are halogen, nitro, alkyl, alkoxy, alkylcarbonyl and alkoxycarbonyl, especially those in which the alkyl groups contain up to 40 carbon atoms, and more preferably up to 30 carbon atoms.

The hydrocarbyl group or groups carried by the ring system, A, are required to give the compound of Formula I good solubility in a non-polar organic solvent, especially the aliphatic and aromatic hydrocarbon solvents which are favoured in metal extraction processs (preferably at least 5 weight % up to complete miscibility) and very low solubility in water (preferably less than 0.01 weight %) and preferably contain a total of from 6 to 30, more preferably 8 to 20, carbon atoms. Examples of hydrocarbyl groups are methyl, ethyl, iso-propyl, butyl, i-pentyl, hexyl, benzyl, phenyl, cyclohexyl and allyl. A preferred hydrocarbyl group is an alkyl, cycloalkyl, alkenyl, aryl group or mixture thereof, especially one containing from 6 to 30, more especially from 8 to 20, carbon atoms and such a group is hereinafter referred to as a lipophilic group. Examples of lipophilic groups are 2-ethylhexyl, octyl, nonyl, i-decyl, tridecyl, 2-hexyldecyl, 2-octyldodecyl, i-octadecyl, benzyl, 4-t-butylbenzyl and 4-dodecylbenzyl. The lipophilic group may be situated anywhere on the ring system and, where X or Y, is C—R or N—R, may be the group R.

A preferred lipophilic group is a $C_{6-30}$-, especially $C_{8-20}$-, aliphatic hydrocarbon chain which may attached directly to the ring system or incorporate a terminal hetero-atom or linking group, such as —O—, —S—, —CO—, —O.CO—, —CO.O—, —SO$_2$—, phenylene, benzylene or —NT—, where T is preferably an inert group, such as H or $C_{1-4}$-alkyl, through which it is attached to the ring system, A. The aliphatic chain may be straight chain but is preferably branched and is desirably a saturated aliphatic group, especially an alkyl group, although this may be interrupted by one or more heteroatoms, especially, O, S or NT, provided, in order to maintain a high hydrophobic to hydrophilic balance in the compound, that there are not more than three such heteroatoms in any lipophilic group. It is, however, preferred that the lipophilic group is branched $C_{8-20}$-alkyl. The compound of Formula I may carry up to three lipophilic groups, which may be the same or different, but preferably carries one or two such groups.

It is not necessary for each molecule to carry the same lipophilic group(s) and the compound of Formula I may conveniently comprise a mixture of compounds of this general formula carrying two or more different lipophilic groups. Such a mixture is conveniently prepared from a starting material comprising a mixture of such lipophilic groups, such as a mixture of isomeric or homologous aliphatic alcohols containing a variety of branched and straight alkyl chains.

A heterocyclic thione in accordance with the first aspect of the present invention can be represented by the Formula II:

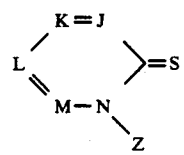  (II)

wherein
(i)
Z is OH; and
J, K, L and M are each independently N or C—R or the group J=K is S, O or N—R, provided there are not more than two N atoms in the ring;
and each R independently is H or a substituent which does not interfere with stripping or extraction; or two groups represented by R on adjacent ring atoms together form a second fused ring;
or (ii)
Z is $R^1$, J is C—OH;

R¹ is H or a substituent which does not interfere with stripping or extraction;

K, L and M are each independently N or C—R or the group L=M is S, provided there are not more than two N atoms in the ring;

and each R independently is H or a substituent which does not interfere with stripping or extraction; or two groups represented by R on adjacent ring atoms together form a second fused ring provided at least one of the groups represented by R is a lipophilic group as hereinbefore defined.

It is preferred that the compound of Formula II is monocyclic and comprises a dihydropyrimidothione or dihydropyridazothione and more especially a dihydropyridothione or a dihydrothiazolothione. In a first preferred compound of Formula II, Z is OH, K is C—R or the group J=K is S; J or L is C—W and the other is C—R and M is C—R, in which W is a lipophilic group as hereinbefore defined. In a second preferred compound of Formula II, Z is a lipophilic group, J is C—OH and K, L and M are C—R.

The first preferred compound can be represented by the Formula III:

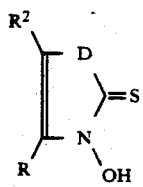
(III)

wherein D is S or CR=CR or CR—CW, R² is R or W, W is a lipophilic group, as hereinbefore defined, and each R is independently H or an inert group as hereinbefore defined provided there is at least one lipophilic group in the molecule. The groups represented by R are H, halogen or $C_{1-4}$-alkyl and the lipophilic group (W) preferably comprises a branched $C_{6-20}$-alkoxycarbonyl group or $C_{6-20}$-alkoxy group.

The second preferred compound can be represented by the Formula IV:

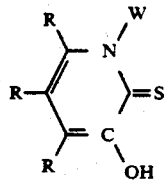
(IV)

wherein W is a lipophilic group, as hereinbefore defined and each of the groups represented by R is H or an inert group as hereinbefore defined. The groups R are preferably H, halogen or $C_{1-4}$-alkyl and the lipophilic group preferably comprises a branched $C_{6-20}$-alkyl or a 4-(t-$C_{6-20}$-alkyl)benzyl group.

Another preferred heterocyclic thione in accordance with the first aspect of the present invention is represented by the Formula V:

(V)

wherein
V is NOH;
and W is NR, S,

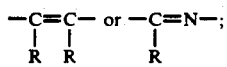

or V is NR;
and W is

in which the COH is adjacent to the thione;

and each R independently is H, or a substituent which does not interfere with striping or extraction provide that at least one R is an aliphatic hydrocarbyl group containing from 8 to 40 carbon atoms.

In the compound of formula (V), it is preferred that one, or at most two, of the groups represented by R is a $C_{8-20}$-alkyl, alkenyl, cycloalkyl, alkyl- cycloalkyl or alkyl-aryl group, which is joined to a nitrogen or carbon atom of the ring either directly or through a nitrogen, oxygen or sulphur atom or through a carbonyl, carboxy, sulphonyl or phenylene group. The remaining groups represented by R are preferably H, halo, $C_{1-4}$-alkyl, $C_{1-4}$-alkoxy, $C_{1-4}$-alkylcarbonyl or $C_{1-4}$-alkoxycarbonyl.

EXTRACTION AND STRIPPING PROCESSES

The compound of Formulas I and II, and more especially the preferred compounds of Formulae III, IV and V have the power to selectively complex with certain metals of Group III and thereby to take them into solution in a non-polar organic solvent, especially an aliphatic hydrocarbon.

Compounds of the invention are extractants for a wide range of metals from aqueous solution. In general metals may be extracted from neutral or weakly acid solution and if required may be then stripped from the loaded organic solution by contacting it with a more strongly acidic aqueous solution to provide a purified solution of the metal or metals. For example silver, copper and mercury are strongly and rapidly extracted and require correspondingly a strongly acidic solution to strip them from the organic solution if it is required to do this. The affinity of the extractants for iron and bismuth is lower, and for zinc, nickel, lead and arsenic, lower still. The indications above are qualitative only: it will be evident to those skilled in the art that by increasing the concentration of the extractant in the organic solution or by raising the pH, the degree of extraction for any particular metal may be increased as required. The extraction or stripping of a metal, M, of valency n, is believed to proceed according to an equilibrium process of the type:

$$n(LH) + M^{n(+)} \rightleftharpoons L_nM + nH^+$$

According to a second aspect of the present invention there is provided a process for the extraction of metal values from solutions of metal salts which comprises contacting the aqueous solution with a solution in a water-immiscible organic solvent of a heterocyclic thione in accordance with the first aspect of the present invention.

The process of the second aspect of the present invention may be applied to the extraction from aqueous solutions of any metal capable of forming a stable complex with the heterocyclic thione. Examples of suitable metals are indium, gallium, silver, copper, mercury, iron, bismuth, zinc, nickel, lead and arsenic. The extractants have very little affinity for chromium, manganese, aluminium and the alkali metals.

Thus, the present process is particularly valuable for the extraction of gallium and/or indium from an aqueous acidic solution containing aluminium, even in a large excess, so as to give an organic solution containing gallium and/or indium which is substantially free of aluminium.

The aqueous solution from which the metals values are extracted may be neutral or acid, but is preferably the latter. However, as the strength of the complex generally decreases with increasing acidity, it is generally prefered that the acidity of the solution is at or above pH 1 and more preferably at or above pH 2. However, the strength of the complex can vary with the structure of the heterocyclic thione and, with certain structures, extraction is feasible at pH <1 and down to 0.5.

As the strength of the metal complexes are pH dependent, and generally weaken with a decrease of pH, the metals can be recovered (stripped) from the complex with the heterocyclic thione by separation of the organic phase from the original aqueous phase and stripping of the metals into an aqueous acid solution.

According to a further feature of the invention there is provided a process for the stripping of a metal from a solution of a complex of the metal with a heterocyclic thione in accordance with the first aspect of the invention in an organic liquid with an aqueous acid solution.

The stripping solution preferably has a higher level of acidity than the solution from which extraction took place. Stripping is generally promoted by a reduction of from 0.25 to 2 pH units, especially from 0.5 to 2 pH unit, but lesser or greater reductions in pH may be employed.

Because the extractant of the present invention has virtually no affinity for aluminium, it is much superior to known extractants, such as derivatives of 8-hydroxyquinoline, because the latter also have affinity for aluminium. Thus, the known extractants are not suitable for the selective extraction of the aforementioned metals, especially gallium and/or indium, from solutions also containing aluminium, especially liquors formed in aluminium preparation processes containing relatively high concentrations of aluminium and low concentrations of metals such as as gallium and indium.

According to a preferred feature of the second aspect of the present invention there is provided a process for the extraction of gallium and/or indium from an aqueous solution of aluminium, gallium and/or indium which comprises contacting the aqueous solution with a solution of a heterocyclic thione according to the first aspect of the present invention in an organic liquid, whereby the gallium and/or indium forms a complex with the heterocyclic thione and is selectively dissolved in the organic liquid.

According to a further feature the gallium and/or indium is stripped from the organic liquid by contacting the organic liquid containing the complex of gallium and/or indium with an aqueous acid solution.

A further valuable property of the extractant is that gallium and indium, in contrast to all the aforementioned metals which form a complex with the heterocyclic ligand can be efficiently stripped from the loaded organic solution by aqueous alkali.

According to a further feature of the present invention there is provided a process for the stripping of gallium and/or indium from a solution of the complex of gallium and/or indium with the heterocyclic thione of the first aspect of the present invention, by contacting the organic solution with an aqueous alkaline solution.

The aqueous alkaline solution preferably contains an alkali-metal or tetralkylammonium hydroxide in slight excess over that necessary to strip the gallium or indium according to the stoichiometry of the equation shown below. Preferably the excess alkali should be sufficient to give an aqueous solution that is 0.1–0.5 molar in alkali after stripping, according to the stoichiometry of the equation, is complete. For example, an organic solution 0.2 molar in gallium can be efficiently stripped with an equal volume of an aqueous solution which 0.9 molar or higher in alkali concentration, or with a smaller volume of an aqueous solution which is correspondingly stronger in alkali content.

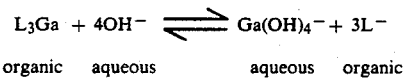

$$L_3Ga\ +\ 4OH^- \rightleftharpoons Ga(OH)_4^-\ +\ 3L^-$$

organic   aqueous        aqueous   organic

By the use of an alkaline stripping solution, gallium and indium can be substantially separated from all the metals and metalloids which may have been co-extracted into the organic liquid. Thus the present process permits the separation of gallium and/or indium from a wide range of impurities, including those which are extractable from an aqueous solution by complexation with the heterocyclic thione, such as silver, copper zinc, etc and those which are not, such as aluminium, chromium, manganese, etc. This comprehensive purification is not possible with the known 8-hydroxyquinoline reagents because these compounds cannot be stripped with alkali: indeed, such extractants complex strongly with gallium in alkaline environment.

ORGANIC LIQUID

A wide range of water-immiscible organic liquids may be used to dissolve the extractant, for example xylene, toluene, chloroform etc. Preferred liquids are high flash-point hydrocarbons favoured by the industry especially substantially aliphatic solvents such as kerosene and ESCAID 100 (a petroleum distillate comprising 20% aromatics, 56.6% paraffins and 23.4% naphthenes commercially available from Esso—ESCAID is a trade mark), and liquids having a higher aromatic content such as AROMASOL H (essentially a mixture of trimethylbenzenes, commercially available from Imperial Chemical Industries PLC—AROMASOL is a trade mark) and SOLVESSO 150 (98% by volume of an aromatic fraction having a boiling range of 190° C. to 210° C., commercially available from Esso—SOLVESSO is a trade mark).

OTHER FEATURES

To improve phase disengagement and promote solubility it can be useful to include modifiers such as aliphatic alcohols e.g. n-decanol or tridecanol in the organic liquid.

It is been found advantageous to include a lipophilic quaternary ammonium or phosphonium salt in the organic liquid to ensure rapid phase-disengagement after contact, especially where the extractant solution is to be stripped with aqueous alkali.

According to a further feature of the present invention there is provided a process for the stripping of a metal from its complex with the heterocyclic thione in an organic liquid, under acid or alkaline conditions, as hereinbefore defined, in which the organic liquid also contains a lipophilic quaternary ammonium or phophonium salt.

Suitable lipophilic quaternary salts are those known to be suitable as phase transfer catalysts e.g. tetrabutyl ammonium bromide or hydroxide, benzyl triethyl ammonium chloride and especially tricapryl methyl ammonium chloride or sulphate. Preferred quaternary salts have at least one lipophilic group containing from 6 to 40 carbon atoms, more especially 6 to 20 carbon atoms. Suitable lipophilic groups are those which have been previously discussed in relation to the lipophilic group present in the heterocyclic thione, and especially alkyl, alkenyl, alkylaryl, cycloalkyl or alkylcycloalkyl groups. The quaternary salt is preferably used in amount equivalent to the extractant, that is 1 mole per mole of extractant or a slightly larger amount. It has been noted that addition of the quaternary salt tends to slightly reduce the strength of the complex between the metal and heterocyclic thione, thus, making it easier to strip.

The heterocyclic thione of the invention is also suitable for absorption onto solid supports to provide ion exchange resins and for inclusion in liquid membranes etc and a support carrying a heterocyclic thione according to the first aspect of the present invention forms a further aspect of the present invention.

It has been noted that a compound of Formula I in which X is N, of Formula II wherein Z=OH, of Formula III or of Formula V wherein V is NOH, in which the hydroxy group is bound to a nitrogen atom, is generally a stronger extractant and, thus, more difficult to strip, than a compound of Formula I in which X is C, of Formula II in which J=C—OH, of Formula IV or of Formula V in which V is NR, although a compound of the latter group, in which the hydroxy group is bound to a carbon atom, is more stable to oxidative decomposition.

EXAMPLES

The invention is illustrated by the following Examples in which all parts and percentages are by weight unless otherwise indicated. In the examples all reported NMR shifts are in parts per million downfield of tetramethylsilane used as internal standard.

EXAMPLE 1

Extractant 1:
1-(4-dodecylbenzyl)-3-hydroxypyridine-2-thione (a) 2-Iodo-3-hydroxypyridine This was prepared from 3-hydroxypyridine as described by Schickh, Binz & Schulz in Berichte [69] 2593 (1936). The product was recrystallised from methanol/water. For $C_5H_4NOI$, % theory (found): C: 27.1 (27.3); H: 1.8 (1.8); N: 6.3 (6.3); I: 57.5 (58.0).

(b) 4-Dodecylbenzyl bromide

This was prepared from commercial mixed-isomer dodecylbenzene as described in Example 1 of U.S. Pat. No. 2,836,626, except that $PBr_3$ was used in the place of $PCl_3$. The product was distilled and the fraction boiling at 170°–182° C./1.5 mm collected.

(c) 3-Hydroxy-2-iodo-1-(4-dodecylbenzyl)pyridinium bromide

A mixture of 3-hydroxy-2-iodopyridine (22.1 g, 0.1M) and 4-dodecylbenzyl bromide (37.2 g, 0.101M) was stirred in sulpholane (100 ml) at 90° C. for 8 hours. Acetone was added and the precipitated product filtered and washed with acetone to yield a white solid (45 g). The product was recrystallised from a mixture of methanol and water, collected and dried at 60° C. (35 g).

(d) 1-(4-dodecylbenzyl)-3-hydroxypyridine-2-thione

3-Hydroxy-2-iodo-1-(4-dodecylbenzyl)pyridinium bromide (35 g) dissolved in a mixture of methanol (80 ml) and water (20 ml) was added to a solution of NaHS.$H_2O$ (7.0 g) in water (20 ml). The mixture was stirred and boiled under reflux for 30 minutes, cooled to room temperature and rotary evaporated to give an aqueous suspension of a pale yellow oil. The oil was extracted with hexane, treated with activated carbon and dried over anhydrous $MgSO_4$. After filtering off the inorganic material the filtrate was rotary evaporated to yield a yellow oil (14.45 g). Microanalysis for $C_{24}H_{35}NOS$, % theory (found): C: 74.8 (74.6); H: 9.1 (9.5); N: 3.6 (3.4); S: 8.3 (8.4).

EXAMPLE 2

Extractant 2:
3-hydroxy-4-methyl-5-n-octylthiazol-2-thione (a) 3-Bromoundecan-2-one A solution of undecan-2-one (170 g, 1.0M) in $CCl_4$ (500 ml) was stirred at 20°–25° C. and bromine (160 g) was added over 15 minutes. The solution decolourised rapidly and stirring was continued for 2 hours at 20°–25° C. when water (100 ml) was added. $NaHCO_3$ (92 g) was added portion-wise and the mixture filtered. The filtrate was dried over anhydrous $MgSO_4$ and distilled. The fraction which boiled at 142°–146° C./20 mmHg (116 g) was collected. NMR($CDCl_3$)=0.7–1.6 (m, 17, $C_8H_{17}$), 2.3 (s, 3, $CH_3$), 4.0–4.4 (t, 1, CH).

(b) 6-Acetyl-4-thio-3-oxa-5-thiatetradecane

This was prepared following the general method described by Bridges & Whitham in JCS (Perkin I) 1603 (1975). Potassium ethyl xanthate (106 g, 0.66M) was stirred in acetone (1 liter) and a solution of 3-bromoundecan-2-one (166 g, 0.66M) added dropwise at 30° C. The mixture was stirred for 18 hours at room temperature, the solid filtered off and the acetone filtrate rotary evaporated to give a pale yellow oil. After dissolving in chloroform, the solution was dried over anhydrous $MgSO_4$, filtered and rotary evaporated to yield a yellow oil (212 g). The product was vacuum distilled with collection of the fraction which boiled at 151°–152° C. (121.86 g). NMR($CDCl_3$)=0.5–1.5 (m, 20, $C_8H_{17}$ and $CH_3$), 2.3 (s, 3, $CH_3$), 4.2–4.5 (t, 1, CH), 4.4–4.8 (q, 2, $CH_2$). M.S. m/z=290.

(c) 6-(1-Oximinoethyl)-4-thio-3-oxa-5-thiatetradecane

This was prepared following the general method described by Barton, Crich & Kretzschmar in JCS (Perkin I) 39 (1986). A solution of 6-acetyl-4-thio-3-oxa-5-thiatetradecane (14.5 g, 0.05M) and hydroxylamine hydrochloride (3.8 g, 0.063M) in dry methanol (50 ml) was stirred at 0° C. and dry pyridine (5.58 g, 0.063M) was added over 15 minutes at 0° C. The mixture was stirred at room temperature for 18 hours and rotary evaporated to yield an oil which was dissolved in diethyl ether (100 ml) and shaken with 2N HCl. The organic solution was washed with water (2×50 ml) and dried over anhydrous $MgSO_4$. After filtering off the inorganic material the filtrate was rotary evaporated to give a pale yellow oil (14.8 g). Microanalysis for $C_{14}H_{27}NO_2S_2$, % theory (found): C: 55.08 (55.5); H: 8.85 (9.0); N: 4.59 (4.8); S: 20.98 (21.4). NMR($CDCl_3$)=0.6–1.6 (m, 20, $C_8H_{17}$ and $CH_3$), 1.9 (s, 3, $CH_3$), 4.2–4.8 (m, 3, $CH_2$ and CH), 9.5 (2, 1, OH). M.S. m/z=305.

(d) 3-hydroxy-4-methyl-5-n-octylthiazol-2-thione

This was prepared following the general method described by Barton, Crich & Kretzschmar in JCS (Perkin I) 39 (1986). A solution of 6-(1-oximinoethyl)-4-thio-3-oxa-5-thiatetradecane (10.5 g, 0.034M) in methylene dichloride (20 ml) was added dropwise over 10 minutes to a vigorously stirred solution of KOH (7.48 g) in water (15 ml) at 0° C. The mixture was stirred for 30 minutes, diluted with water and acidified by dropwise addition of 35% HCl. The organic phase was washed with water (2×100 ml), dried anhydrous $MgSO_4$, filtered and the filtrate rotary evaporated to yield a green-yellow oil (6.68 g). Microanalysis for $C_{12}H_{21}NOS_2$, % theory (found): C: 55.56 (56.3); H: 8.16 (8.9); N: 5.40 (4.5); S: 24.72 (23.0). M.S. m/z=259. NMR($CDCl_3$)=0.6–1.8 (m, 17, $C_8H_{17}$), 2.2(s, 3, $CH_3$), 9.15 (s, 1, OH).

EXAMPLE 3

Extractant 3:
1-hydroxy-5-(2-hexyldecyloxycarbonyl)pyridine-2-thione (a) 2-Chloro-5-(2-hexyldecyloxycarbonyl)pyridine A suspension of 6-chloronicotinic acid (47.4 g, 0.3 mol) in xylene (150 ml) containing DMF (1.5 ml) was stirred and heated at 80° C. whilst $SOCl_2$ (26.1 ml, 0.36 mol) was added during 20 minutes. Stirring and heating at 80° C. was continued for 1½ hours, when all had passed into solution. Excess $SOCl_2$, HCl, and a little xylene were then removed by distillation at 20 mm pressure. The residual solution was cooled to 40° C., and 2-hexyldecanol (72.9 g, 0.3 mol) was added during 20 minutes, the temperature rising to 55° C.

The solution was stirred at ambient temperature for 18 hours, heated for 45 minutes at 60° C., and then distilled, the fraction bp 195° C./0.2 mmHg (55.7 g) being collected. Microanalysis for $C_{22}H_{36}NO_2Cl$, % theory (found): C: 69.18 (70.1); H: 9.50 (10.2); N: 3.67 (3.7); Cl: 9.28 (10.2). NMR($CDCl_3$)=0.7–1.5 (m, 31, $CH_2$, $CH_3$), 4.25 (d, 2, $OCH_2$), 7.35 (d, 1, ArH), 8.25 (q, 1, ArH), 8.95 (d, 1, ArH). M.S. m/z=391.

(b) 2-chloro-5-(2-hexyldecyloxycarbonyl)pyridine-N-oxide

The product from Stage (a) (45.8 g, 0.12 mol) was dissolved in dichloromethane (350 ml) and trifluoroacetic acid (60 ml) was added dropwise during 30 minutes. $H_2O_2$ (100 vol, 31 ml, 0.24 mol) was then added during 15 minutes and the solution was boiled under reflux for 4 hours. A further addition of $H_2O_2$ (5 ml) was made and boiling was continued for a further 5 hours when it was shown by TLC ($SiO_2$, $CHCl_3$:$CH_3CO_2C_2H_5$=1:1) that only a trace of starting material remained. The mixture was poured onto ice and the organic solution was extracted with aqueous sodium carbonate and water, dried ($MgSO_4$) and concentrated at 0.2 mm pressure to 46 g of oil. Microanalysis for $C_{22}H_{36}NO_3Cl$, % theory (found): C: 66.39 (66.2); H: 9.12 (9.5); N: 3.52 (3.2); Cl: 8.91 (8.7). M.S. m/z=397. NMR($CDCl_3$)=7.65 (m, 2, ArH), 8.90 (2, 1, ArH), otherwise as starting material.

(c) 1-hydroxy-5-(2-hexyldecyloxycarbonyl)pyridine-2-thione

The product of Stage (b) (39.8 g, 0.1 mol) was dissolved in ethanol (360 ml) and water (40 ml). NaHS (15 g, 0.2 mol) was added and the mixture was stirred and boiled under reflux for 1 hour. The mixture was cooled, diluted with water (500 ml) and extracted with 10% $NaCO_3$ solution and twice with water, then dried ($MgSO_4$) and concentrated at 0.2 mmHg pressure to a brown oil (42.1 g). It was expected in this way to obtain the product as the sodium salt (calculated for Na 5.51%), but analysis showed it to be mainly in the free-acid form. Microanalysis for $C_{22}H_{37}NO_3S$, % theory (found): C: 66.79 (66.4); H: 9.42 (9.9); N: 3.54 (3.2); S: 8.10 (9.2); Na: 0.00 (0.9); Cl: 0.00 (>0.2) %. M.S. m/z=395, but m/z=379 and 756 also present. NMR($CDCl_3$)=0.6–1.7 (m, 31, $CH_2$/$CH_3$), 4.1 (m, 2, CH), 7.43 (bs, 2, ArH), 8.9 (bs, 1, ArH).

EXAMPLE 4

Extractant 4:
1-hydroxy-3-[2-(1,3,3-trimethylbutyl)-5,7,7-trimethyloctoxy]pyridine-2-thione(1-hydroxy-3-iso-octyldecoxypyridine-2-thione)

(a) 2-Chloro-3(iso-octyldecoxy)pyridine

Iso-octadecyl bromide was prepared from commercial 2-(1,3,3-trimethylbutyl)-5,7,7-trimethyloctanol (Hoechst). Pearl NaOH (8.7 g, 0.218 mol) and iso-octadecyl bromide (72 g, 0.218 mol) were added to a stirred solution of 2-chloro-3-hydroyxpyridine (23.3 g) in DMF (150 ml). The solution was stirred and heated at 65°–70° C. for 36 hours during which time a little KI was added as a catalyst, and a further addition of NaOH (0.9 g) was made. The reaction mixture was extracted into hexane and the hexane solution was extracted several times with water, concentrated and distilled.

2-Chloro-3-iso-octadecoxypyridine (33.8 g) was collected at 165° C./0.3 mmHg pressure. M.S. m/z=382. NMR($CDCl_3$)=0.5–1.5 (m, 35, $CH_2$, $CH_3$), 3.9 (d, 2, $OCH_2$), 7.12 (d, 2, ArH), 7.92 (t, 1, ArH).

(b) 2-Chloro-3-iso-octadecoxypyridine-N-oxide

To a solution of the product of Stage (a) (19.1 g) in dichloromethane (125 ml), trifluoroacetic acid (25 ml) followed by 100 vol $H_2O_2$ (12.5 ml) were added dropwise. The solution was boiled under reflux for 1 hour, allowed to cool, treated with a further 3 ml of H₂O₂ and boiled for a further 2 hours when conversion of the starting material was complete (by TLC). The solution was cooled and poured into ice and water and extracted with ethyl acetate. The ethyl acetate solution was extracted twice with 1M Na₂CO₃ solution and twice with water, dried (MgSO₄) and concentrated finally at 70° C. and 0.5 mm pressure (19.3 g). M.S. m/z=397. NMR(CDCl₃)=6.95 (m, 2, ArH), 7.96 (d, 1, ArH), otherwise as precursor.

(c) 1-Hydroxy-3-iso-octadecoxypyridine-2-thione

A solution of the product of Stage (b) (17.9 g) in ethanol (180 ml) and water (20 ml) was boiled under reflux for 2 hours with NaHS (6.7 g) when conversion of the starting material was complete (by TLC). The solution was cooled, diluted with hexane (150 ml) and ethyl acetate (150 ml), extracted with Na₂CO₃ solution and twice with water, dried (MgSO₄) and concentrated finally at 70° C. and 0.5 mm pressure (2.2 g). Microanalysis for $C_{23}H_{41}NO_2S$, % theory (found): C: 69.82 (68.7); H: 10.45 (10.3); N: 3.35 (3.2). M.S. m/z=395. NMR(CDCl₃)=3.85 (d, 2, OCH₂), 6.68 (m, 2, ArH), 7.78 (m, 1, ArH), otherwise as precursors.

EXAMPLE 5

Extraction of various metals

An aqueous solution containing 250–350 ppm (parts per million w/v) of Ag I, Bi III, Cr III, Cu II, Fe III, Hg II, Mn II, Ni II, Pb II and Zn II was made up by dissolving the metal acetates in water (except for Cr, Ag, Bi which were taken as nitrates). This solution was contacted by stirring (400–700 rpm), at organic:aqueous phase ratio of 1 (O:A=1) and ambient temperature, with a 0.1 molar solution of the Extractant to be tested in SOLVESSO 150/n-decanol (9:1 v/v). During contact the pH was adjusted when necessary to the required value by dropwise addition of a small volume of aqueous 1M NaOH. After 18–24 hours the slurry was allowed to separate, the pH of the aqueous phase was recorded, and both the liquid phases were analysed for metals. The percentage of the total of each metal present which had been extracted into the organic phase is listed in Table 1. For purposes of calculation a metal concentration was taken as zero if it was below the detection limit i.e. less than 2.5 ppm.

TABLE 1

| | % Extraction of Various Metals | | | | | | |
|---|---|---|---|---|---|---|---|
| | Extractant | | | | | | |
| | 1 | | 2 | | 3 | | 4 |
| Metal | pH 3.3 | pH 2 | pH 3 | pH 2 | pH 3 | pH 2 | pH 3 |
| Ag | 100 | 100 | 100 | 100 | 100 | 100 | 100 |
| Bi | 95 | 94 | 100 | 100 | 100 | 100 | 100 |
| Cr | 0 | 0 | 2 | 0 | 3 | 2 | 4 |
| Cu | 100 | 100 | 100 | 100 | 100 | 100 | 100 |
| Fe | 100 | 69 | 100 | 98 | 99 | 99 | 98 |
| Hg | 100 | 100 | 100 | 100 | 100 | 100 | 100 |
| Mn | 0 | 0 | 0 | 0 | 0 | 0 | 1 |
| Ni | 0 | 0 | 99 | 25 | 85 | 49 | 98 |
| Pb | 2 | 0 | 100 | 100 | 97 | 88 | 100 |
| Zn | 6 | 0 | 100 | 95 | 95 | 82 | 100 |

EXAMPLE 6

Rate and Extent of Extraction of Gallium from Aqueous Solution

An acidic aqueous feed solution, simulating that obtainable from Bayer Liquor by a primary extraction process, was prepared by dissolving gallium nitrate, aluminium sulphate and sodium sulphate in 0.1M H₂SO₄ and found by analysis to contain 1.25 g/l (1250 ppm) Ga, 10.3 g/l Al and 26.4 g/l Na. This solution was contacted by stirring at 600–800 rpm at 25° C., at the O:A phase ratio listed in Table 2, with the organic solution of the Extractant made up as in Example 5 (except that for Extractant 1 the molarity of the Extractant was 0.25 rather than 0.1). During contact, the pH of the slurry was maintained at 3.3 by automatic addition of aqueous 1M NaOH as demanded by a glass electrode immersed in the slurry. Samples of the slurry were removed periodically at times up to 48 hr, allowed to separate and analysed for Ga, Al and Na. The percentages of the total gallium which were extracted into the organic phase after this time are listed in Table 2, together with the times required to reach 50% (T₅₀) and 90% (T₉₀) of this final value which were estimated graphically. No sodium or aluminium were detected in the organic phase.

TABLE 2

| Extractant | Molarity | O/A ratio | T₅₀ | T₉₀ | % Ga Extracted after 48 hours |
|---|---|---|---|---|---|
| 1 | 0.25 | 1/3 | 11 hr | 40 hr | 66% |
| 2 | 0.1 | 1/2 | 24 min | 3 hr | 96% |
| 3 | 0.1 | 1/2 | 9 min | 39 min | 100% |
| 4 | 0.1 | 1/2 | 57 min | 4 hr | 88% |

EXAMPLE 7

Stripping with mineral acid solutions

A 0.1 molar solution of the extractant as described in Example 5 was loaded with gallium by contacting it with an aqueous solution of gallium nitrate to give the organic gallium concentration listed in Table 3. Aliquots of the organic solution were then contacted by stirring, with equal volumes of water, 0.1M HCl and 1M HCl respectively for periods long enough for equilibrium to be attained (as indicated by the rate-data obtained from Example 6). The aqueous and organic solutions were allowed to separate and were analysed. The percentages of the gallium initially present in the organic solution which had been stripped into the aqueous solution are recorded in Table 3.

TABLE 3

| Extractant | Initial gallium concentration | % of Gallium stripped by: | | |
|---|---|---|---|---|
| | | Water | 0.1M HCl | 1.0M HCl |
| 1 | 900 ppm | 3.4 | 98.7 | — |
| 2 | 1700 ppm | 0.3 | 17.0 | 87.6 |
| 3 | 2425 ppm | 0.04 | 6.4 | 41.7 |
| 4 | 1750 ppm | 0.06 | 0.2 | 95.1 |

EXAMPLE 8

This demonstrates the separation of gallium from a range of metallic impurities by extraction and subsequent stripping into dilute alkali, and the use of a quaternary ammonium salt to improve phase disengagement during alkaline stripping.

An extractant solution which was approximately 0.12 molar in ALIQUAT 336 and 0.1 molar in Extractant 2 was prepared by dissolving Extractant 2 (5.18 g, strength by titration 50% of theoretical, MW 259) and ALIQUAT 336 (4.46 g) in ESCAID 100/n-decanol (9:1 v/v) and diluting with the same solvent mixture to 100 ml.

An aqueous feed solution was prepared by mixing feed solutions prepared as described for Examples 5 and 6 so as to give the compositions listed in Row 1 of Table 4.

The extractant and feed solutions (each 95 ml) were contacted by stirring at 600 r.p.m. for 5 hours during which time the pH was adjusted to 3.0 and maintained at this value by addition of 1M NaOH solution (8.8 ml required). The solutions were allowed to separate and the organic solution was filtered (Whatman 'Phase Sep' paper), and stripped by stirring (600 r.p.m.) at an organic/aqueous phase ratio of 2.0 for 45 minutes with a solution prepared by dissolving 2.07 g of 'ARISTAR' NaOH in distilled water and diluting to 100 ml. The solutions were allowed to separate and the aqueous solution (purified extract) was filtered and analysed with the results given in Row 2 of Table 4. In this example, aluminium and mercury were not determined. The results show that within experimental area the theoretical amounts of gallium had been recovered from a solution containing a large excess of aluminium and at the same time purified from a range of metallic impurities to below the detection limits of the analytical method used.

EXAMPLE 9

The procedure of Example 8 was repeated except that the organic solution contained 0.1 moles/liter of Extractant 4 rather than Extractant 2. This solution (145 ml) was contacted with 217.5 ml of the aqueous feed solution so as to give an O/A phase ratio of 0.667, and 16.9 ml of 1M NaOH were required to reach and maintain pH 3.0 during extraction. As before, stripping was carried out at an O/A phase ratio of 2. Results are given in Row 3 of Table 4. It was shown by analysis of the loaded organic solution that about 70% of the available gallium had been extracted and that, within experimental error, all the gallium extracted had been stripped.

TABLE 4

| Solution | Metal Concentrations (ppm) | | | | | | | | | | | |
|---|---|---|---|---|---|---|---|---|---|---|---|---|
| | Ga | Al | Ag | Bi | Cr | Cu | Fe | Hg | Mn | Ni | Pb | Zn |
| Aqueous Feed | 1125 | 9300 | 31 | 23 | 28 | 30 | 24 | 27 | 30 | 31 | 36 | 31 |
| Purified Extract (Ex 8) | 2190 | — | <0.1 | <0.1 | <0.1 | <0.1 | <0.1 | — | <0.1 | <0.1 | <0.5 | <0.1 |
| Purified Extract (Ex 9) | 2370 | 3.0 | <0.1 | <0.5 | <0.2 | <0.1 | <0.1 | <0.2 | <0.1 | <0.2 | <0.5 | <0.1 |

We claim:

1. A process for extracting metal values from an aqueous solution of metal salts whereby said process comprises contacting said aqueous solution with a solution comprising a water immiscible organic solvent having dissolved therein a heterocyclic thione of the formula:

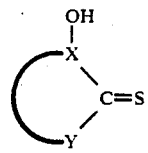

wherein:
X is C and Y is N—R;
or X is N and Y is C—R, N, N—R, O or S;
each R is independently H or a substituent which does not interfere with stripping or extraction; and
A is a mono- or bi-cyclic system, which includes the group —X(OH)—CS—Y—, and which carries one or more aliphatic hydrocarbyl groups containing a total of from 6 to 40 carbon atoms.

2. The process of claim 1 whereby a metal heterocyclic thione complex is formed as a result of contacting said aqueous solution containing metal value with said water immiscible organic solvent having dissolved therein a heterocyclic thione and subsequently stripping the metal from the solution containing the metal heterocyclic thione complex by the step which comprises contacting said metal heterocyclic thione complex with an aqueous acid solution which has a higher level of acidity than the solution from which the extraction took place.

3. The process of claim 1 wherein the aqueous solution contains gallium and/or indium in the presence of aluminium.

4. The process of claim 1 wherein the aqueous solution contains gallium and/or indium and wherein the process includes the subsequent step of stripping of gallium and/or indium from the solution of the complex of gallium and/or indium with the heterocyclic thione in the water-immiscible organic solvent by contacting the organic solution with an aqueous alkaline solution which contains an alkali-metal or tetralkylammonium hydroxide in slight excess over that necessary to strip the gallium or indium.

5. The process of claim 1 in which the water-immiscible organic solvent includes a lipophilic quaternary ammonium or phosphonium salt.

6. A process in accordance with claim 1 wherein said heterocyclic thione is 3-hydroxy-4-methyl-5-n-octyl-thiazol-2-thione.

* * * * *